United States Patent
Friezner

(10) Patent No.: US 10,995,484 B2
(45) Date of Patent: *May 4, 2021

(54) STORM WATER GATE WITH SENSORS

(71) Applicant: Denis Friezner, Cathedral City, CA (US)

(72) Inventor: Denis Friezner, Cathedral City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/857,002

(22) Filed: Apr. 23, 2020

(65) Prior Publication Data

US 2020/0256046 A1 Aug. 13, 2020

Related U.S. Application Data

(63) Continuation of application No. 16/164,494, filed on Oct. 18, 2018, now Pat. No. 10,648,165.

(51) Int. Cl.
*E03F 5/04* (2006.01)
*G01N 1/10* (2006.01)
*G01N 33/18* (2006.01)

(52) U.S. Cl.
CPC .......... *E03F 5/0411* (2013.01); *E03F 5/0401* (2013.01); *G01N 1/10* (2013.01); *G01N 33/1813* (2013.01); *G01N 33/1826* (2013.01); *G01N 2001/1043* (2013.01); *G01N 2033/184* (2013.01)

(58) Field of Classification Search
None
See application file for complete search history.

(56) References Cited

U.S. PATENT DOCUMENTS

| | | | |
|---|---|---|---|
| 3,945,746 A | 3/1976 | Bredbenner | |
| 7,234,894 B1 | 6/2007 | Flury | |
| 7,611,304 B2 | 11/2009 | Lill et al. | |
| 7,951,291 B2 | 5/2011 | Nino | |
| 8,535,523 B2 * | 9/2013 | Friezner | F15D 1/0005 |
| | | | 210/156 |
| 8,945,375 B2 * | 2/2015 | Friezner | E03F 5/0404 |
| | | | 210/131 |
| 9,428,899 B2 * | 8/2016 | Friezner | E03F 5/0404 |
| 10,648,165 B1 * | 5/2020 | Friezner | G01N 1/18 |
| 2012/0103883 A1 * | 5/2012 | Friezner | F15D 1/0005 |
| | | | 210/156 |
| 2014/0041744 A1 * | 2/2014 | Friezner | F15D 1/0005 |
| | | | 138/39 |
| 2015/0053598 A1 * | 2/2015 | Friezner | E03F 5/0404 |
| | | | 210/156 |
| 2020/0123757 A1 * | 4/2020 | Friezner | G01N 33/1826 |
| 2020/0256046 A1 * | 8/2020 | Friezner | E03F 5/0411 |

* cited by examiner

*Primary Examiner* — Robert J Popovics
(74) *Attorney, Agent, or Firm* — James E. Brunton

(57) ABSTRACT

A fluid flow control and debris intercepting apparatus for controlling the flow of fluid and the introduction of debris into the entrance of a conventional curbside storm drain of the character having spaced apart side walls that define a fluid flow channel through which fluid flows. Additionally, the apparatus senses the nature and extent of contaminants contained within the fluid.

10 Claims, 7 Drawing Sheets

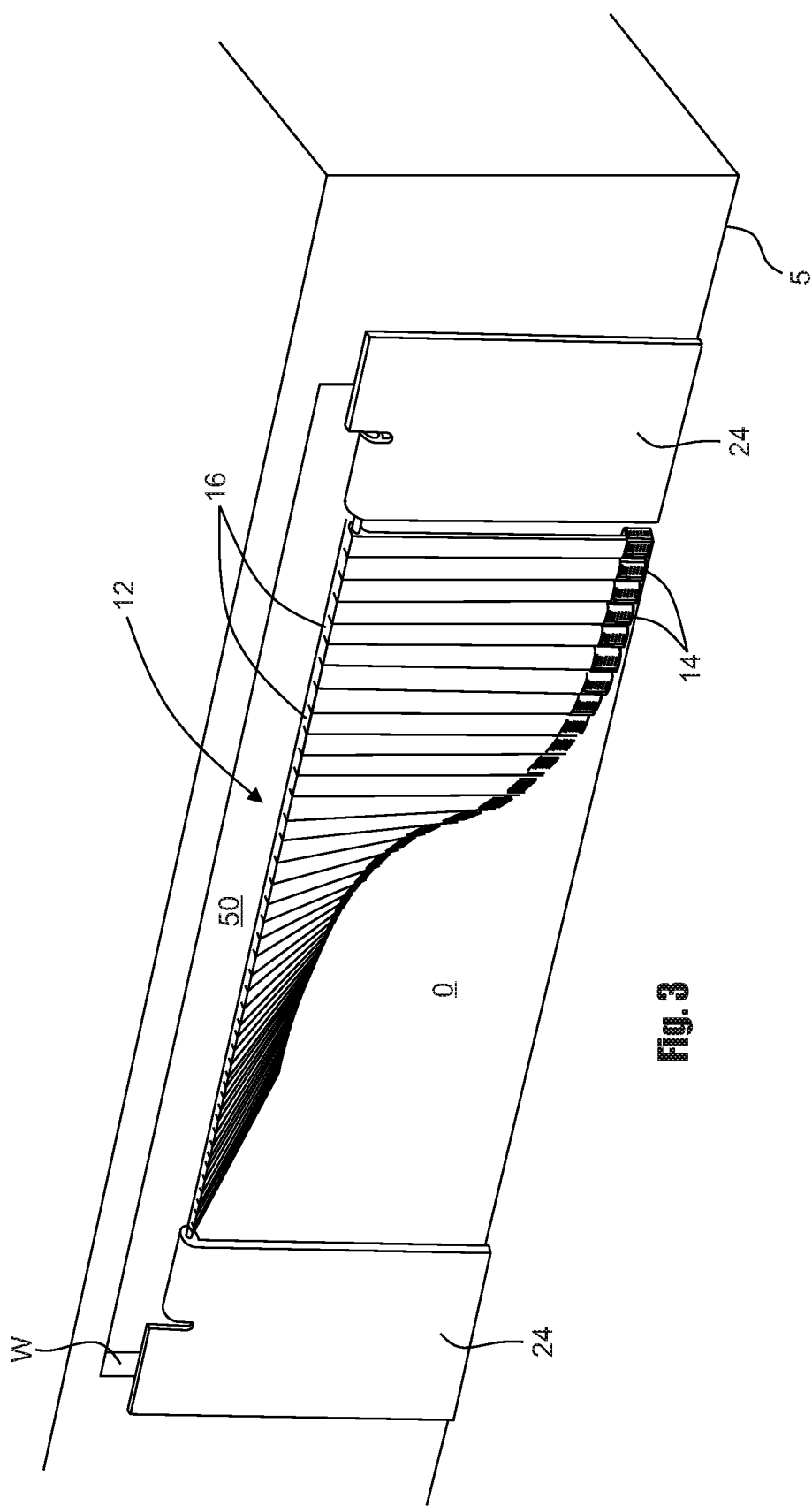

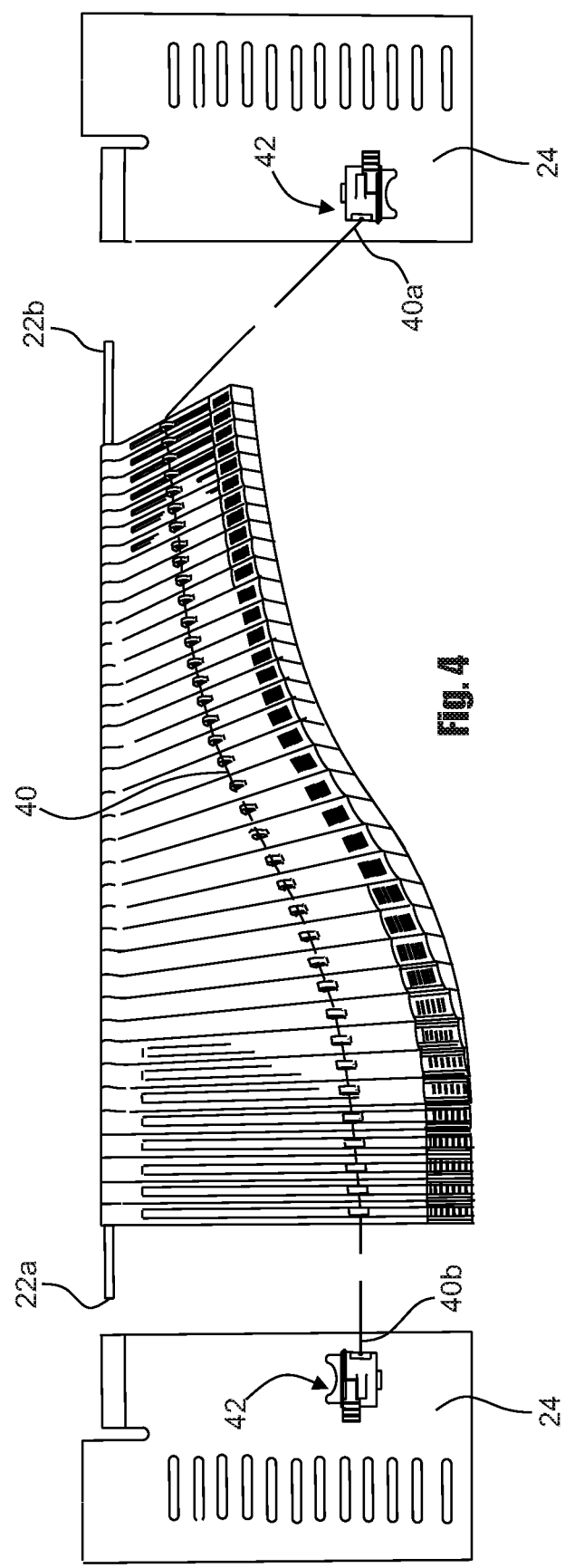

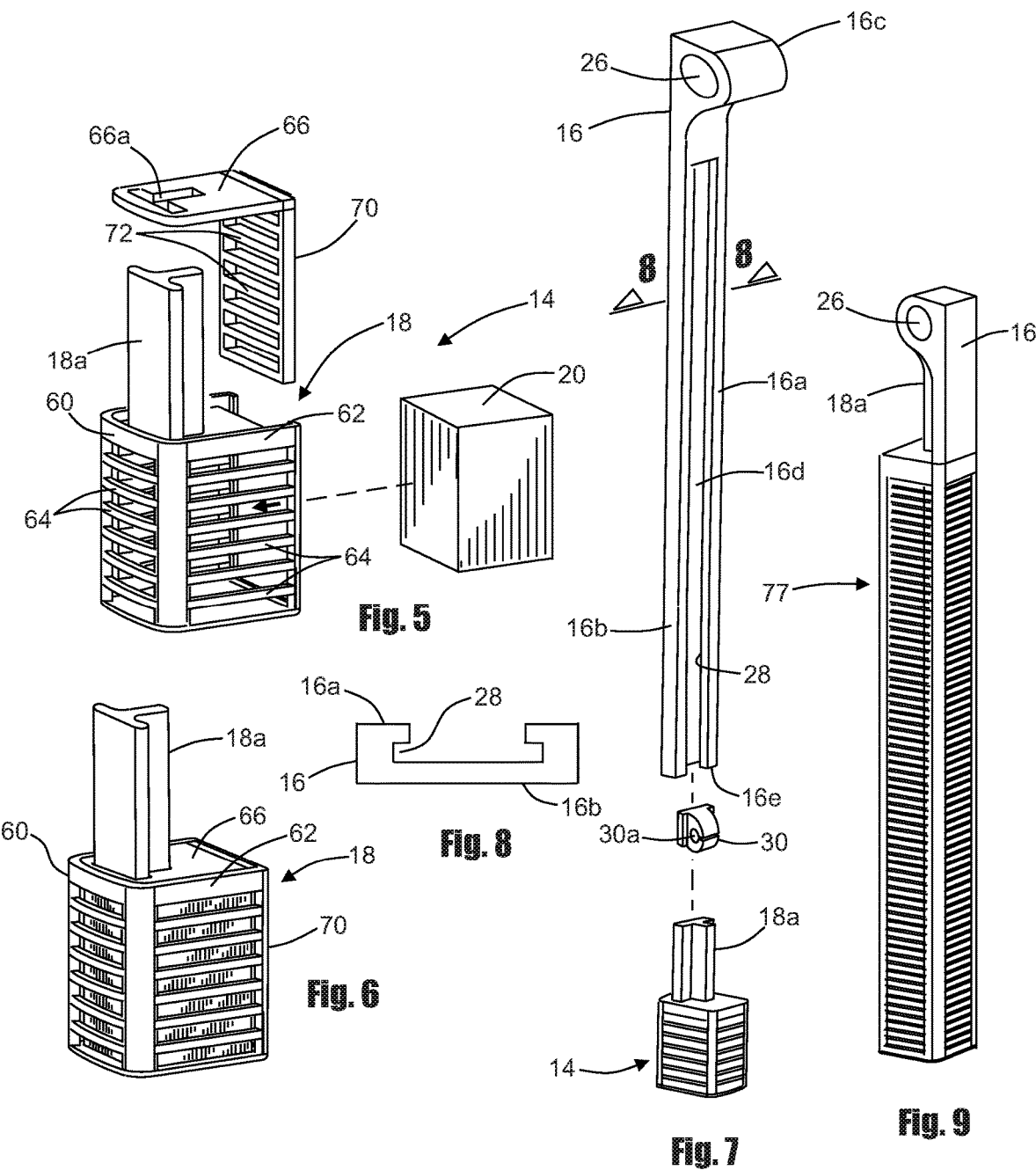

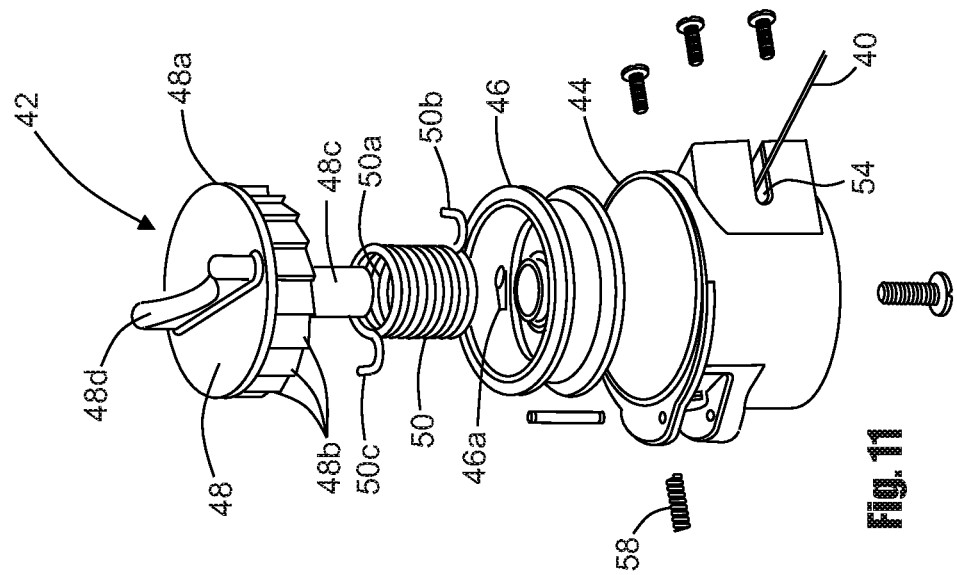
Fig. 11
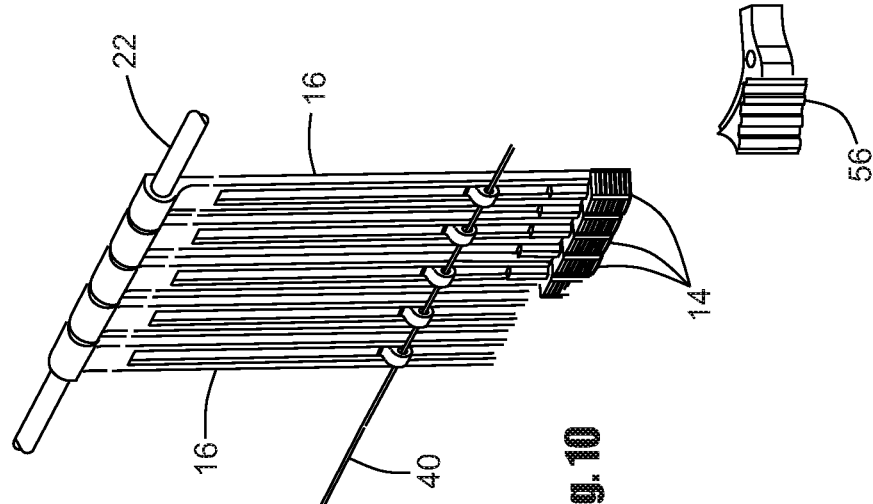
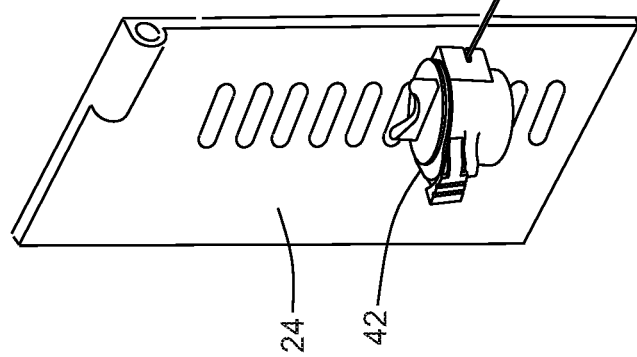
Fig. 10

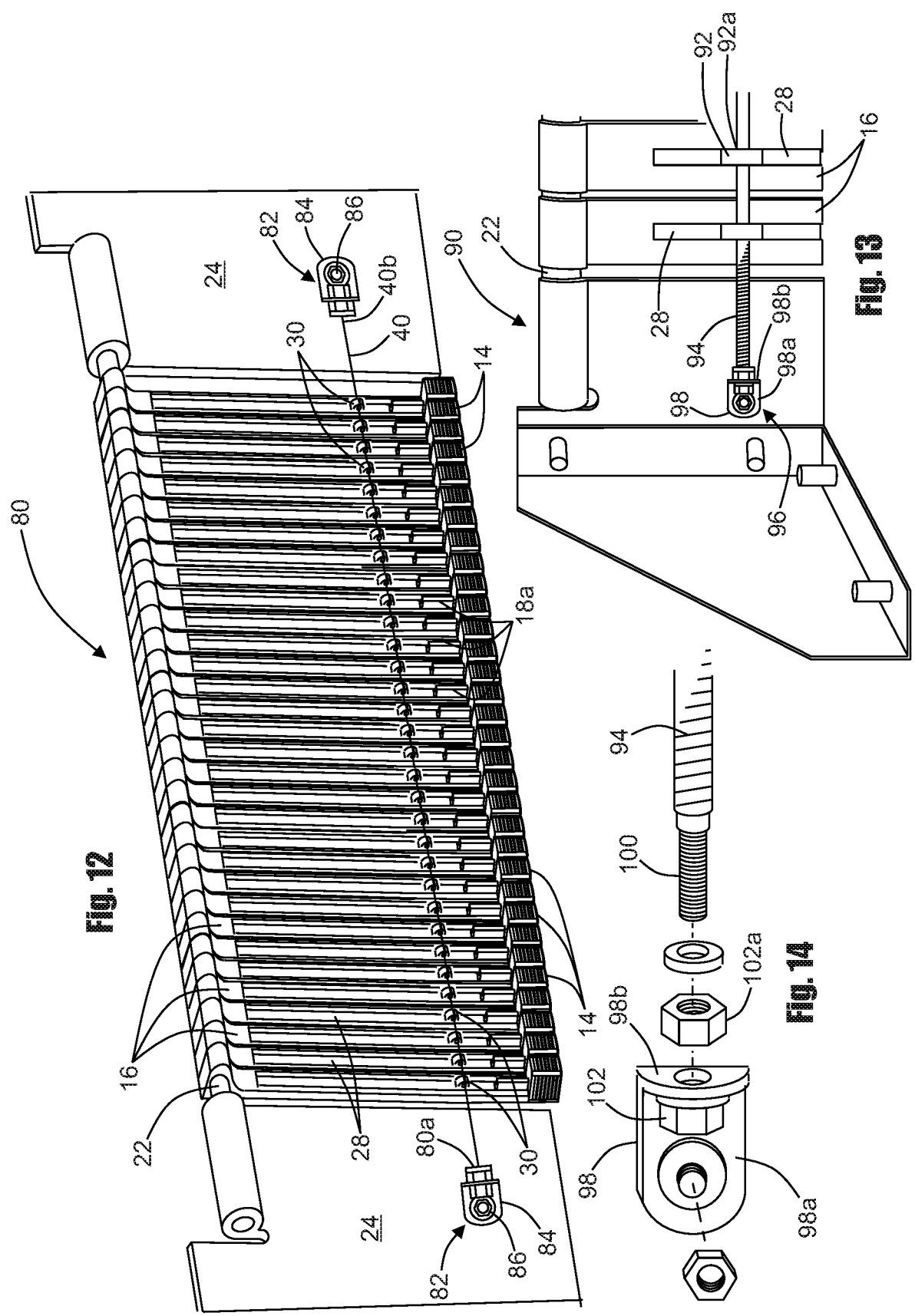

STORM WATER GATE WITH SENSORS

CROSS-REFERENCE TO RELATED APPLICATIONS

This is a Continuation application of U.S. Ser. No. 16/164,494 filed Oct. 18, 2018.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

Field of the Invention

The present invention relates generally to storm water control systems. More particularly, the invention concerns a storm water gate for controlling the flow of fluid and the introduction of debris into the entrance of a water diversion system and for sensing the nature and extent of contaminants contained in the fluid.

Description of Related Art Including Information Disclosed Under 37 CFR 1.97 and 1.98

The control of excess runoff rain water has long been a problem faced by municipalities throughout the civilized world. Heavy rainfall can create large volumes of runoff that must be handled effectively in order to avoid flooding, that can result in road closures and substantial property damage. Accordingly, most municipalities have installed drain systems that include curbside drains that are provided at spaced apart locations along most thoroughfares. The curbside drains typically lead to main drain pipes that carry the water to adjacent rivers, directly to the ocean, or to remote catch basins.

While the prior art drain systems have, for the most part, proven effective in carrying runoff storm water away from the streets and populated areas, the control of man-made and natural debris entering the drain systems remains a major problem. For this reason, various attempts have been made in the past to prevent unwanted debris from entering into curbside drains. These prior art attempts have included placing plates over the drains that are specially configured to trap the debris and still provide limited space for the water to flow. This approach has generally proven unsatisfactory because, as a general rule, the drains cannot adequately accommodate the runoff during heavy rainfall events. Other attempts have been made to design curbside drain gates that remain closed during dry periods, but open during moderate to heavy rainfall events.

A novel and highly successful fluid flow control and debris intercepting apparatus is described in U.S. Pat. No. 8,535,523 in which the inventor of the present application is named as a co-inventor. The present invention, which is an improvement over the invention disclosed in the U.S. Pat. No. 8,535,523, not only controls the fluid flow into the entrance of a water diversion system, but also senses the nature and extent of contaminants contained within the fluid. Because of the pertinence of U.S. Pat. No. 8,535,523, this patent is hereby incorporated by reference as though fully set forth herein.

U.S. Pat. No. 3,945,746 issued to Bredbenner illustrates another prior art approach to wastewater flow control and discloses a specially configured catch basin curb inlet opening cover that comprises a rectangular grating panel that is adapted to be supported in a stationary frame surrounding and opening of a storm drain inlet. U.S. Pat. No. 7,611,304 issued to Lill et al. illustrates another prior art approach to providing a specially configured catch basin curb inlet opening cover.

U.S. Pat. No. 7,234,894 issued to Flury discloses an automatically openable and closable gate system for use with street side curb openings that includes a gate which during dry and low flow water drainage situations is in a closed position and during periods of heavy rainfall will automatically open. U.S. Publication No. 2008/0226390 discloses a system that is somewhat similar to the Flury system and includes an automatic fluid channel screen lock-unlock system for automatically locking and unlocking a screen that is disposed within a fluid channel wherein the screen is rotatable relative to the channel from a closed position to an open position.

BRIEF SUMMARY OF THE INVENTION

By way of brief summary, the present invention comprises a fluid flow control and debris intercepting apparatus for controlling the flow of fluid and the introduction of debris into the entrance of a conventional curbside storm drain of the character having spaced apart side walls that define a fluid flow channel through which fluid flows. However, the present invention not only controls the fluid flow into the entrance of a water diversion system, but also senses the nature and extent of contaminants contained within the fluid.

In one form of the invention the apparatus comprises an elongated, yieldably deformable support in the form of a cable under tension that substantially spans the fluid flow channel and a plurality of transversely spaced apart flow control vanes that are connected to the cable. The flow control vanes function to control fluid flow through the curbside drain and work in tandem to block the entry of unwanted debris into the storm drain. To accomplish this purpose, the flow control vanes are pivotally movable between a first at rest position and a second position wherein an increase in fluid flow through t e fluid flow channel is permitted. The system further includes a mechanism for controlling the tension in the elongated, yieldably deformable support cable and thereby controlling the resistance that is offered by the system to the flow of fluid through the fluid flow channel and the entry of objects into the storm drain. Additionally, the system of the present invention, not only controls the fluid flow in to the entrance of a water diversion system, but also senses the nature and extent of contaminants contained within the fluid flowing into the water diversion system. In one form of the invention, this contamination sensing function is accomplished by providing each of the flow control vanes with sample collection assembly that comprises a collection container and a sample collecting media. Preferably, the sample collecting media comprises a material capable of removing from the fluid flowing through the fluid flow channel contaminants selected from the group consisting of hydrocarbons, including fertilizers and wastes from humans and animals, heavy metals and pesticides.

With the forgoing in mind, it is an object of the present invention to provide an apparatus that effectively controls the flow of fluid and the introduction of unwanted debris into the entrance of a curbside storm drain.

Another object of the invention is to provide an apparatus of the character described that senses the nature and extent of contaminants contained within the fluid flowing into the water diversion system.

Another object of the invention is to provide an apparatus as described in the preceding paragraph that functions to sense contaminants contained within the wastewater selected from the group consisting of hydrocarbons, including fertilizers and wastes from humans and animals, heavy metals and pesticides.

Another object of the invention is to provide an apparatus of the aforementioned character that can readily be installed by unskilled workmen in storm drains of varying standard and nonstandard construction, including curbside storm drains and storm drains provided in temporary concrete highway barriers such as "K rails".

Another object of the invention is to provide an apparatus of the aforementioned, character that effectively prevents the entry of unwanted debris into curbside storm drains during conditions of low to moderate rainfall, but may permit the free entry of debris into the storm drain during conditions of heavy rainfall.

Another object of the invention is to provide an apparatus of the class described that can be specially tailored to accommodate directional fluid flow as, for example, downhill fluid flow.

Another object of the invention is to provide an apparatus of the described in the preceding paragraph which, because of its unique design, cannot jam and will automatically open to permit fluid flow through the flow control channel when the flowing water impinges upon control vanes.

Another object of the invention is to provide an apparatus as described in the preceding paragraphs that is easy to install and in no way affects the structural integrity of the storm drain.

Another object of the invention is to provide an apparatus of the class described in which the flow control vanes of the apparatus can be readily modified for use in storm drains of varying height and width.

Another object of the invention is to provide an apparatus of the class described in the preceding paragraph which, because of the unique design of the lightweight flow control vanes of the apparatus, permits a significantly higher flow volume of water through the fluid flow channel than is permitted by prior art devices embodying perforated flow control gates.

Another object of the invention is to provide an apparatus as described in the preceding paragraphs that is easily adjustable to accommodate varying fluid flow conditions.

Another object of the invention is to provide an apparatus of the class described that is durable in use and one that can be inexpensively manufactured, installed and maintained.

BRIEF DESCRIPTION OF SEVERAL VIEWS OF THE DRAWINGS

FIG. 3 is a generally perspective front view of the control gate portion of the fluid flow control and debris intercepting apparatus as it appears with the control gate in an open position.

FIG. 4 is a generally perspective rear view of the fluid flow control and debris intercepting apparatus shown in FIG. 1 as it appears with the control gate in an open position.

FIG. 5 is a greatly enlarged, generally perspective, exploded view of one of the sample collection assemblies of the invention of the character that is connected to the lower extremities of the flow control vanes of the control gate.

FIG. 6 is a generally perspective view of the sample collection assembly shown in FIG. 5 as it appears in an assembled configuration.

FIG. 7 is a greatly enlarged, generally perspective, exploded view of one of the flow control vanes of the invention and of the sample collection assembly that is connected to the lower extremity thereof.

FIG. 8 is a cross-sectional view taken along lines 8-8 of FIG. 7.

FIG. 9 is a greatly enlarged, generally perspective view of an alternate form of flow control vane and sample collection assembly that is connected thereto.

FIG. 10 is an enlarged, generally perspective fragmentary exploded view of part of the left-hand portion of FIG. 4 further illustrating the construction of the control gate and the cable tensioning system of the invention.

FIG. 11 is a greatly enlarged, generally perspective, exploded view of one form of the cable tensioning device of the invention.

FIG. 12 is a generally perspective rear view of an alternate form of the fluid flow control and debris intercepting apparatus of the invention.

FIG. 13 is a fragmentary, generally perspective rear view of still another form of the fluid flow control and debris intercepting apparatus of the invention.

FIG. 14 is a greatly enlarged, generally perspective exploded view of the tension spring member swivel connector assembly shown in the lower left hand portion of FIG. 13.

DETAILED DESCRIPTION OF THE INVENTION

Figure 1:
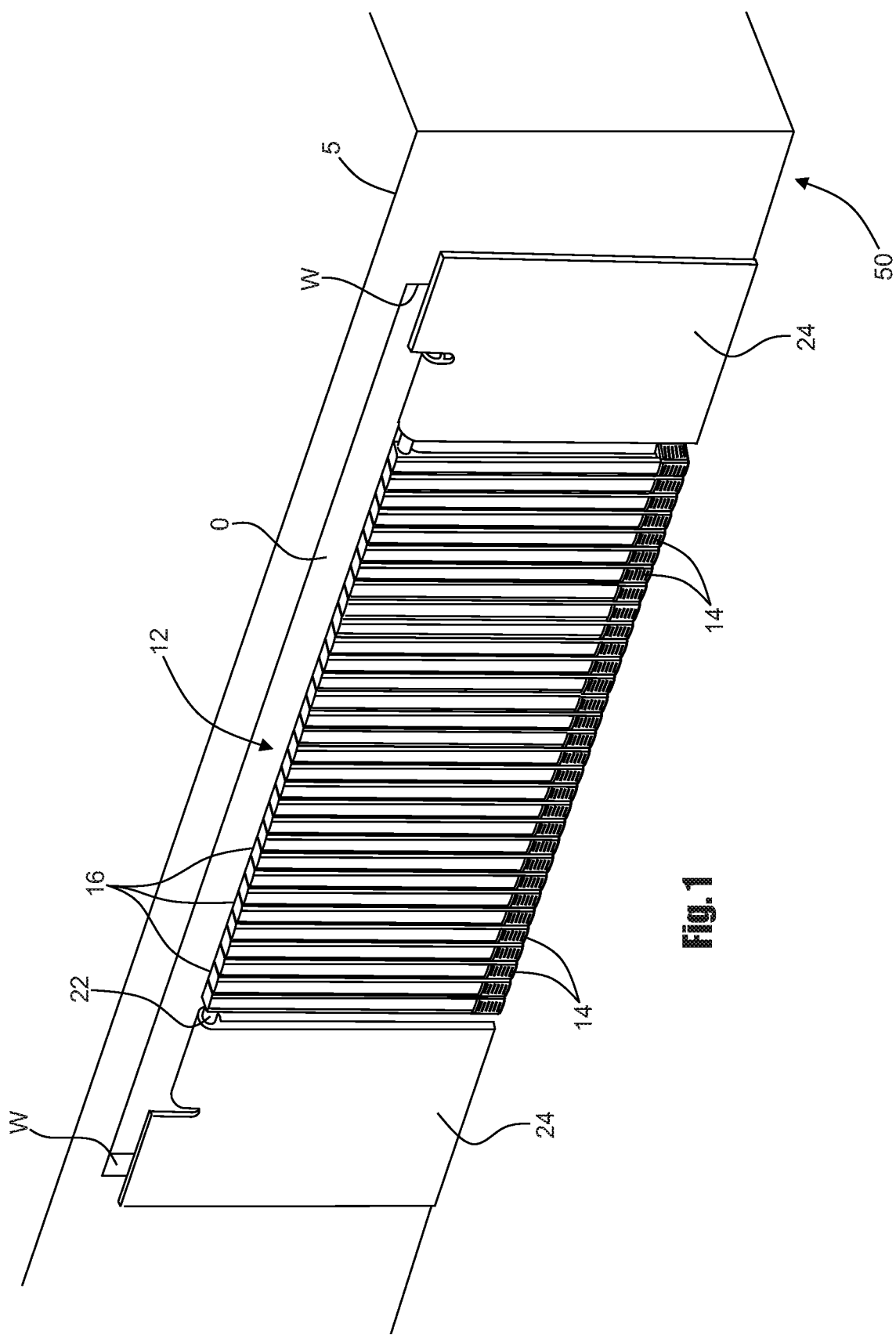
FIG. 1 is a generally perspective front view of one form of the fluid flow control and debris intercepting apparatus as it appears when installed in a storm drain.
Figure 2:
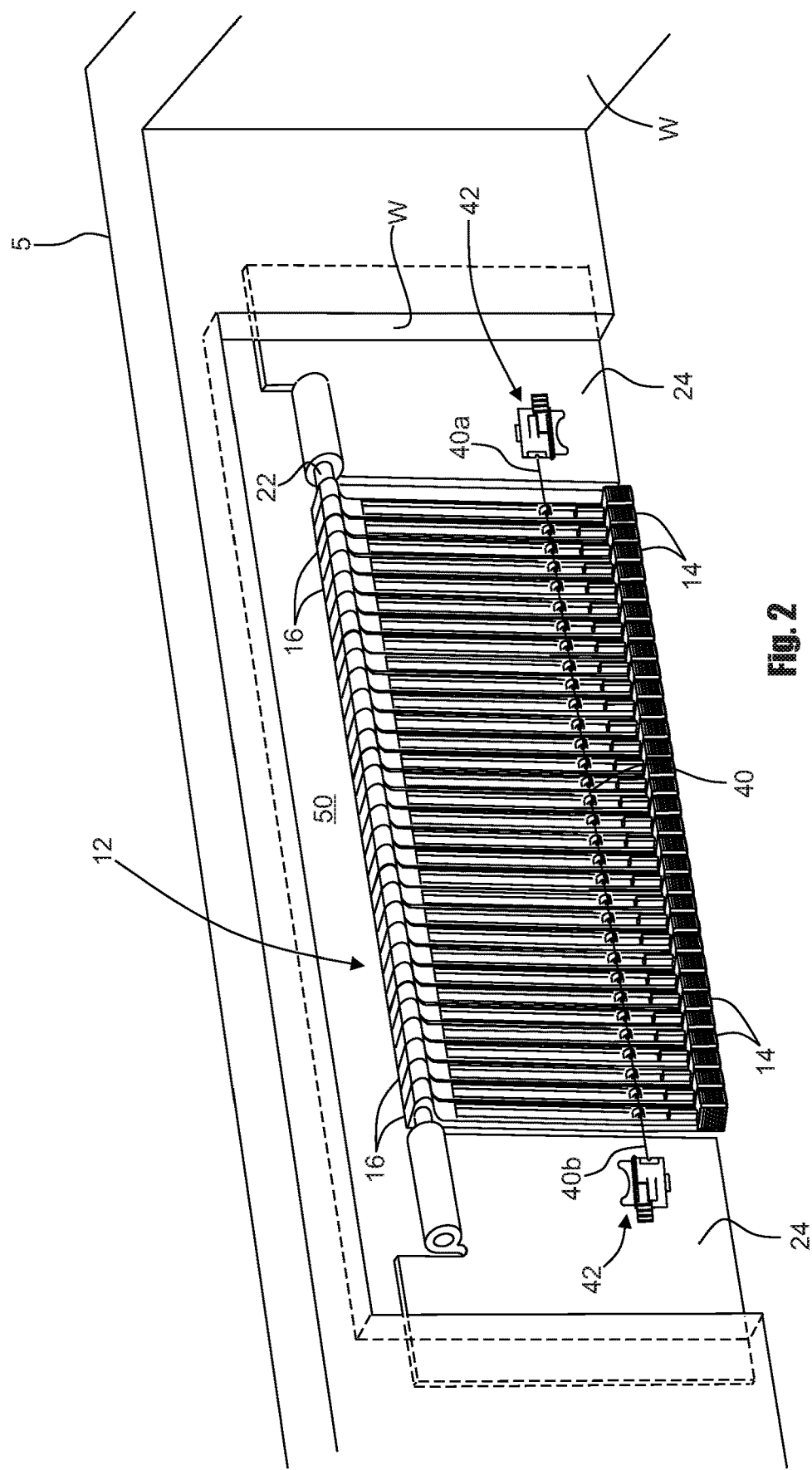
FIG. 2 is a generally perspective rear view of the fluid flow control and debris intercepting apparatus shown in FIG. 1.

Referring to the drawings and particularly to FIGS. 1 and 2, one form of the fluid flow control, analysis and debris intercepting apparatus of the invention is there shown as it appears when positioned within a storm drain opening. This embodiment of the apparatus, which is generally designated in the drawings by the numeral 12, functions to control the flow of fluid and the introduction of debris into the opening "O" of the storm drain "SD" that comprises a structure "S" having spaced apart side walls "W" that define the opening "O" through which fluid, such as rainwater flows. As will be discussed in greater detail in the paragraphs that follow, this embodiment of the invention also uniquely includes a plurality of sample collection assemblies 14 that are connected to uniquely configured flow control vanes 16, the construction and function of which will be described in greater detail in the paragraphs which follow. As best seen in FIGS. 5 and 6 of the drawings, each of the collection assemblies comprises a collection container 18 and a sample collecting media 20. Collecting media 20 can be made up of a wide variety of materials, but preferably comprises a material selected from the group consisting of activated carbon, polypropylene and absorbent cellulose.

In the form of the invention shown in FIGS. 1 through 4, the apparatus 12 comprises a support member 22 to which the flow control vanes 16 are pivotally connected. Support member 22, which comprises an elongated, generally cylindrically shaped pivot rod having first and second extremities 22a and 22b (FIG. 4), is connected to side mounting members 24, which are in turn connected to structure "S" in the manner shown in FIG. 1 of the drawings.

Flow control vanes 16 uniquely function to control fluid flow through the fluid flow channel and to selectively block the entrance of debris into the channel. As illustrated in FIGS. 7 and 8 of the drawings, each of the flow control vanes 16 has a front face 16a, a rear face 16b, an upper portion 16c, an intermediate portion 16d and a lower extremity 16e. The upper portion 16c of each of the flow control vanes is provided with a transverse bore 26 that is constructed and arranged to slidably receive the support member 22. The front face of each of the flow control vanes is provided with a generally U-shaped groove 28 that is adapted to slidably receive a guide member 30 having a transverse bore 30a. (FIG. 7). Groove 28 is also adapted to slidably receive the mounting column portion 18a of each of the collection containers 18 of the collection assemblies 14.

Also forming an important aspect of the present invention is an elongated, biasing member, shown here as an elongated, yieldably deformable biasing cable 40 (FIGS. 2 and 4) having a first end 40a and a second end 40b. Cable 40 is received within openings 30a formed in the guide members 30 (see FIG. 7). Cable 40 uniquely functions to controllably resist movement of the vanes toward their second position. In a manner presently to be described, cable 40 is continuously maintained in tension and the degree of tension in the cable is regulated by a novel tensioning mechanism 42 that is carried by the structure "S". As best seen in FIGS. 9 and 10, this important tensioning mechanist here comprises a hollow housing 44, a cable retaining cup 46 disposed within housing 44 for rotation with respect thereto and a finger engaging ratchet wheel 48 connected to the housing for rotation with respect thereto. As illustrated in FIG. 11 of the drawings, finger engaging ratchet wheel 48 has a peripheral portion 48a provided with a multiplicity of circumferentially spaced apart teeth 48b and a central stem 48c that extends outwardly therefrom. Stem 48c extends through the central opening 50a of a conventional torsion spring 50 that is mounted within cable retaining cup 46. Torsion spring 50 has a first end 50b that is connected to the cable retaining cup 46 and a second end 50c that is connected to finger engaging ratchet wheel 48.

After the tensioning mechanism 42 has been connected to the side mounting panels 24 in the manner shown in FIG. 10, the end of the biasing cable 40 can be fed through the receiving slot 54 formed in the housing 44 in the manner shown in FIGS. 10 and 11. This done, the end of the biasing cable can be fed through the receiving slot 46a formed in the cable retaining cup 46 and suitably interconnected with the cable retaining cup. With this construction, tension can be applied to the biasing cable 40 by grasping the finger engaging bar 48d of the ratcheting wheel and rotating the ratcheting wheel 48 against the urging of torsion spring 50. To release tension on the biasing cable 40, a ratchet release pawl 56 is pivotally connected to housing 44 in the manner illustrated in FIG. 11 of the drawings. The ratchet release pawl is movable between a first position wherein the teeth 56a on the pawl engage the teeth 48b preventing rotation of said finger engaging ratchet wheel and a second position permitting rotation of said finger engaging ratchet wheel. A conventional coil spring 58 functions to releasably maintain the release pawl in its first position.

In using the apparatus of the invention, the cable 40 is first tensioned in the appropriate manner by rotating the finger engaging knob 48 of the tensioning mechanism, which is operably associated with spring 50. As the water flows through the fluid flow channel and impinges on the control vanes 16, the control vanes will tend to move in the manner shown in FIGS. 3 and 4 of the drawings. However, since the control vanes are interconnected with the cable 40, the cable will yieldably resist the movement of the control vanes. It is apparent that the degree of tension placed on the cable 40 controls the amount of force that must be imparted on the control vanes by the flowing fluid to move the cable into the configuration shown in FIG. 4. The greater the tension on the cable 40, the greater is the force against the fluid flowing through the storm drain "SD" and impinging on the control vanes that is required to move the cable into an arcuate configuration as is illustrated in FIG. 4 and to move the control gate into an open position. Conversely, the lesser the tension on the cable 40, the lower is the force against fluid flowing through the storm drain "SD" and impinging on the control vanes that is required to move the control gate into an open position. With this in mind, during periods of heavy rainfall when it is desired to encourage maximum fluid flow through the storm drain, a lesser tension is placed on the cable 40 so that the control gate can open widely to permit maximum fluid flow and also to permit debris, such as plastic bottles and the like that may build up against the control gate to flow freely into the storm drain. However, during periods of light rainfall when it is desired to accommodate the light rainfall, but at the same time to prevent debris from entering the storm drain, a greater tension is placed on the cable 40 so as to prevent the control gate from opening wide enough to permit the debris to move past the control gate and enter into the storm drain.

Turning now to FIGS. 5 through 8 of the drawings, it can be seen that the collection container 18 of each of the collection assemblies of the invention comprises interconnected front and side walls 60 and 62 which include vertically spaced apart slats 64. Connected to and spanning side walls 60 and 62 is a top wall 66. Connected to top wall 66 and extending upwardly there from is the previously mentioned mounting column 18a that is generally T-shaped in cross-section. The sample collecting media 20, which is disposed within the collection container, is held in position by a rear wall 70 that includes vertically spaced apart slats 72. Connected to the rear wall 70 and extending outwardly there from is the top wall 66 that is provided with a generally T-shaped opening 66a through which mounting column 18a is slidably received in the manner shown in FIG. 6. It is to be observed that the spaced apart slats 64 and 72 provided on the walls of the collection container define a plurality of fluid ports that permit fluid flow into the connecting container in a manner to uniformly wet the collecting media 20 that is disposed within the container.

As previously mentioned and as illustrated in FIGS. 7 and 8 of the drawings, in operation the mounting column portion 18a of each of the collection assemblies 14 is slidably received within the generally U-shaped groove 28 formed in the front face of each of the flow control vanes 16. With this construction, the collection containers and the sample collecting media 20 disposed there within is strategically positioned in the path of the wastewater flowing through the fluid flow channel.

Turning next to FIG. 9 of the drawings, an alternate form of collection assembly and sample collecting media of the invention is there shown. This form of the collection assembly and sample collecting media, which is designated by the numeral 77, is similar in construction and operation to the embodiment shown in FIGS. 5 through 8. However, as indicated in FIG. 9, it is of a greater length so that it can be more effectively used in flow channels of greater depth.

Referring now to FIG. 12 of the drawings, still another form of the fluid flow control and debris intercepting apparatus of the invention is there shown as it appears when positioned within a conventional curbside storm drain. This form of the apparatus, which is generally designated in the drawings by the numeral 80, functions to control the introduction of fluid and debris into the entrance of a conventional storm drain. Apparatus 80 is similar in many respects to the embodiment of the invention shown in FIGS. 1 through 8 and like numerals are used in FIG. 12 to identify like components. The primary difference between this latest form of the invention and that of the previously described invention resides in the provision of tensioning mechanisms that are of a different construction and operation from the tensioning mechanisms 42 of the embodiment of the invention shown in FIGS. 1 through 8.

As before, the apparatus includes a plurality of sample collection assemblies 14 that are connected to uniquely configured flow control vanes 16, which are, in turn, pivotally connected to a support member 22. Support member 22 is connected to side mounting members 24, which are connected to structure "S" in the manner shown in FIG. 1 of the drawings. As in the earlier described embodiment of the invention, the front face of each of the flow control vanes is provided with a generally U-shaped groove 28 that is adapted to slidably receive a guide member 30 having a transverse bore 30a (FIG. 7). Groove 28 is also adapted to slidably receive the mounting column portion 18a of each of the collection containers 18 of the collection assemblies 14 (FIG. 5). An elongated, yieldably deformable biasing cable 40 having first and second ends 40a and 40b is received within openings 30a formed in the guide members 30 (see FIG. 7).

Cable 40 functions to controllably resist movement of the vanes toward their second position and is continuously maintained in tension by swivel connector assemblies 82 that are mounted on side mounting members 24. As illustrated in FIG. 12, the ends 40a and 40b of cable 40 are securely connected to connector assemblies 82 by a suitable means. More particularly, the cable end portions are connected to an angle bracket 84 that is rotatably connected to the side mounting members 24 by a threaded connector 86. With this construction, as the water flowing through the storm drain moves the vanes out of their vertical plane and into their second, displaced configuration as illustrated in FIG. 4, the angle brackets 84 will rotate relative to the side mounting members 24 and in so doing will function to effectively regulate the tension on the cable 40.

Turning next to FIGS. 13 and 14 of the drawings, yet another form of the fluid flow control and debris intercepting apparatus of the invention is there shown. This form of the apparatus, which is generally designated in the drawings by the numeral 90, is similar in many respects to the embodiments of the invention shown in FIGS. 1 through 8 and 12 and like numerals are used in FIGS. 13 and 14 to identify like components. The primary differences between this latest form of the invention and that of the previously described invention resides in the absence of the sample collection assemblies and the provision of a totally different biasing mechanism for controlling movement of the vanes toward their second position.

In this latest form of the invention, the apparatus comprises a plurality of uniquely configured flow control vanes 16, which are pivotally connected to a support member 22. Support member 22 is connected to side mounting members 24, which are in turn connected to structure "S" in the manner shown in FIG. 1 of the drawings. As in the earlier described embodiments of the invention, the front face of each of the flow control vanes is provided with a generally U-shaped groove 28 that is here adapted to slidably receive a guide member 92 having a transverse bore 92a.

Forming an important aspect of this latest form of the invention is the previously mentioned tensioning member, here provided as an elongate tension spring member 94 having first and second end portions that are secured to side mounting members 24 by means of novel swivel connector assemblies 96. Tension spring members 94 are readily commercially available from various sources including the Jones spring Co. Inc. of Wilder Ky. These spring members, which can be provided in various diameters ranging from ⅛ to ⅜ inches in diameter, have proven to be suitable for the purposes of the present invention.

As best seen in FIG. 14 of the drawings, each of the swivel connector assemblies 96, which connect the spring members to the side mounting members 24, include an angle bracket 98 the first leg 98a of which is rotatably connected to the mounting member 24 by a threaded connector 86 and the second leg 98b of which extends perpendicularly outward from the mounting, member (FIG. 14). The ends of the tension spring member 94 are removably connected to the second leg 98b of the angle bracket by any suitable means such as elongate threaded studs 100 and mating connector nuts 102 and 102a. More particularly, as best seen in FIG. 14 of the drawings, threaded studs 100 have a first end connected to the tension spring member and a second end connected to the angle brackets by means of the connector nuts 102 and 102a. With this construction, the degree of tension in the spring member is regulated and controlled by the swivel connector assemblies as the first legs 98a of the angle brackets rotate relative to the side mounting members 24 due to the movement of the control vanes out of plane and toward their second positions as a result of liquid flowing through the flow channel (see FIG. 4).

The selection of a suitable tension spring member 94 for use in a particular storm drain configuration is accomplished in accordance with the method of the invention described in the paragraphs which follow.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention as set forth in the following claims.

I claim:

1. A fluid flow control, analysis and debris intercepting apparatus for controlling flow through a structure having an opening defining a fluid flow channel and for analyzing contaminants contained within the fluid flow, said apparatus comprising:
(a) a support member connected to the structure and spanning the fluid for channel;
(b) a plurality of transversely spaced apart flow control vanes carried by said support member for controlling fluid flow through the fluid flow channel, each of said flow control vanes being movable between a first position and a second position permitting an increase in the volume of fluid flow through the fluid flow channel; and (c) a sample collection assembly connected to a selected one of said flow control vanes, said collection assembly comprising a sample collecting media.

2. The apparatus as defined in claim 1 in which said sample collection assembly further comprises a container for containing said sample collecting media.

3. The apparatus as defined in claim 1 in which said sample collecting media comprises a material capable of removing contaminants from the fluid flowing through the fluid flow channel.

4. The apparatus as defined in claim 1 in which said sample collecting media comprises an absorbent cellulose material.

5. The apparatus as defined in claim 1 in which said sample collecting media comprises activated carbon.

6. The apparatus as defined in claim 1 further including a yieldably deformable biasing member connected to each of said flow control vanes for resisting movement of each of said flow control vanes toward said second position.

7. The apparatus as defined in claim 6 in which said yieldably deformable biasing member comprises a yieldably deformable, elongate cable.

8. The apparatus as defined in claim 6 further including a tensioning mechanism carried by the structure and connected to said biasing member for controlling the tension in said biasing member.

9. apparatus as defined in claim 8 in which said tensioning mechanism comprises a torsion spring operably associated with said biasing member.

10. The apparatus as defined in claim 8 in which said tensioning mechanism comprises:

(a) a hollow housing connected to said structure;
(b) a cable retaining cup disposed within said housing for rotation with respect thereto;
(c) a ratchet wheel connected to said housing for rotation with respect thereto; and
(d) a torsion spring disposed within said housing, said torsion spring having a first end connected to said cable retaining cup and a second end connected to said ratchet wheel.

* * * * *